Figure 1:
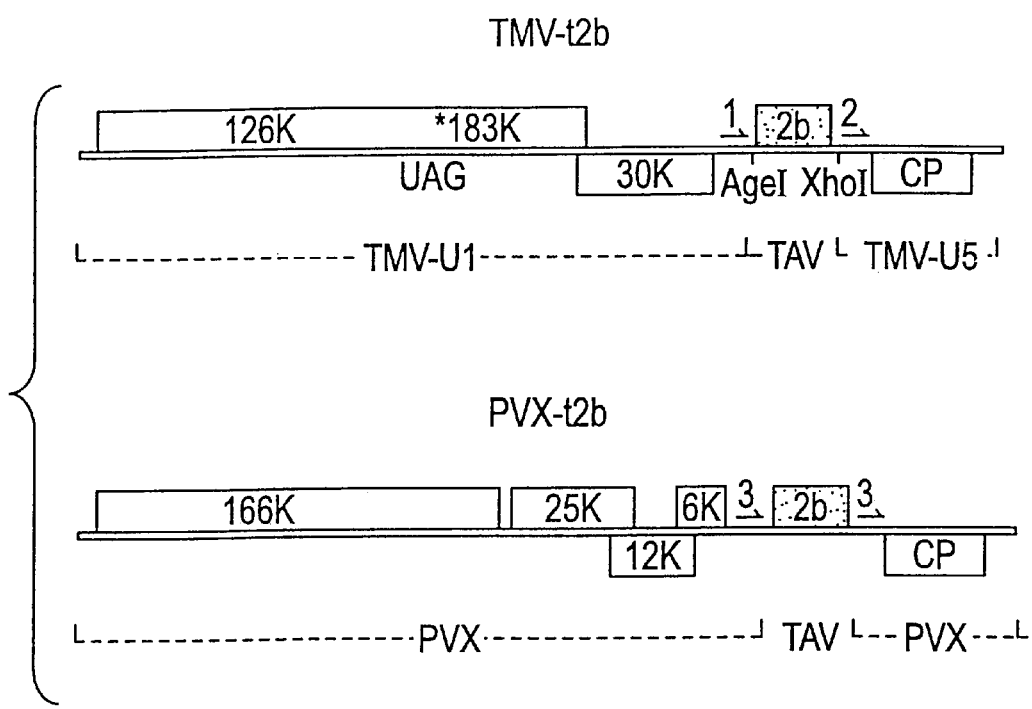

US006207882B1

(12) United States Patent
Ding

(10) Patent No.: US 6,207,882 B1
(45) Date of Patent: Mar. 27, 2001

(54) DISEASE RESISTANT TRANSGENIC PLANTS COMPRISING A TOMATO ASPERMY VIRUS 2B GENE

(76) Inventor: Shou-Wei Ding, 360 Pasir panjang Road Goldcoast Condominium #04-09, Singapore (SG)

( * ) Notice: Subject to any disclaimer, the term of this patent is extended or adjusted under 35 U.S.C. 154(b) by 0 days.

(21) Appl. No.: 09/153,241

(22) Filed: Sep. 15, 1998

(51) Int. Cl.[7] .............................. A01H 5/00; A01H 5/10; C12N 15/82

(52) U.S. Cl. ........................ 800/301; 435/320.1; 800/280

(58) Field of Search ................................ 435/69.1, 320.1, 435/419, 468; 536/23.72; 800/280, 279, 301, 320.1, 320.2, 320.3, 320, 317, 306, 317.4, 317.1, 312, 317.3, 309, 310, 317.2, 314

(56) References Cited

PUBLICATIONS

De Block M. "The cell biology of plant transformation: Current state, problems, prospects and the implications for the plant breeding." Euphytica 71: 1–14, 1993.*

Ross, Systemic acquired resistance induced by localized virus infections in plants[1], *Virology* 14, 340–358 (1961).

Malamy et al., Temperature–dependent induction of salicylic acid and its conjugates during the resistance response to tobacco mosaic virus infection. *The Plant Cell*, 4, 359–366 (1992).

Metraux et al., Increase in salicylic acid at the onset of systemic acquired resistance in cucumber. *Science*. 250, 1004–1006 (1990).

Ward et al., Coordinate gene activity in response to agents that induce systemic acquired resistance. *The Plant Cell*,3, 1085–1094 (1991).

Ding et al., New overlapping gene encoded by the cucumber mosaic virus genome[1]. *Virology*, 198, 593–601 (1994).

Shi et al., In vivo expression of an overlapping gene encoded by the cucumoviruses. *J. Gen. Virol.*, 78, 237–241 (1997).

Cornelissen et al., Structure of tobacco genes encoding pathogenesis–related proteins from the PR–1 group, *Nucleic Acids Research*, vol. 15, No. 17, 6799–6811 (1987).

Chapman et al., *Plant J.*, vol. 2, 549–557 (1992).

* cited by examiner

*Primary Examiner*—Amy J. Nelson
(74) *Attorney, Agent, or Firm*—Rothwell, Figg, Ernst & Manbeck

(57) ABSTRACT

Transgenic plants transformed with a tomato aspermy virus 2b gene or active fragment thereof exhibit resistance to diseases caused by infectious pathogens, such as viruses. Expression of the 2b gene causes activation of hypersensitive response and expression of pathogenicity-related proteins in plants that are incapable of such a response to certain pathogens. Transformation of a wide variety of plants with expression vectors in which the tomato aspermy virus 2b gene is operably linked to a plant-active promoter renders the plant resistant to pathogenic infection.

19 Claims, 2 Drawing Sheets

DISEASE RESISTANT TRANSGENIC PLANTS COMPRISING A TOMATO ASPERMY VIRUS 2B GENE

BACKGROUND OF THE INVENTION

1. Field of the Invention

The present invention relates to methods and materials for conferring disease resistance to plants. More particularly, the invention relates to transgenic plants containing a heterologous nucleic acid which confers disease resistance, particularly against infectious pathogens, such as viruses. The invention further relates to methods and materials for preparation of such transgenic plants.

Infectious diseases of cultivated plants cause substantial reductions in food, forage and fiber throughout the world. Control of these diseases has been based primarily on cultural practices that include removal of infected debris, eradication of weed hosts (herbicide applications), prevention of vector transmission (pesticide applications), indexing for pathogen-free starting material (seed or vegetative propagules) and breeding for disease resistance. Large scale methods for curing plants once they have become infected with viruses do not exist. Thus, the control of diseases is dependent upon methods to prevent or delay the establishment of infection.

Of the above disease control measures, breeding for resistance is generally one of the most economical and practical methods, as it requires no additional labor or expense to the grower. Moreover, controlling diseases with resistance does not require applications of herbicides or pesticides to eliminate weed hosts and insect vectors. Thus, host resistance is one of the most environmentally safe and durable methods for controlling plant diseases. Unfortunately, in many plant-virus systems, resistance is not available and cannot be obtained using traditional plant-breeding strategies. However, recent advances in molecular biology and gene manipulation have proven helpful in integrating new disease resistance factors into plant-virus systems where none existed before.

2. Background Art

The development of transgenic plants has proven to be a valuable strategy for protecting plants from viral diseases. For example, Stubbs, G. et al., U.S. Pat. No. 5,723,750 describe transgenic plants expressing genes encoding wild-type and modified coat proteins of different virus groups. These transgenic plants have been shown to have varying levels of resistance to infection by the corresponding virus. Unfortunately, the expression of heterologous genes encoding coat proteins does not confer broad resistance to viral infections and has no effect on pathogenesis caused by other infectious agents.

An important mechanism of a plant's resistance to a pathogenic infection is the hypersensitive response ("HR"). During the HR, the recognition of a pathogen induces a rapid cell death process that results in the formation of a zone of dead cells (necrosis) around the site of infection. This HR lesion is believed to inhibit further spread of the pathogen and to generate a signal that activates host defense mechanisms and, in many cases, induces long-lasting systemic resistance to a broad spectrum of pathogens (Ross, 1961). (A bibliography is provided at the end of the written description.) Induction of such systemic resistance is termed systemic acquired resistance (SAR) and is accompanied by an increase in the rate of synthesis of several pathogenesis-related (PR) proteins and the accumulation of salicylic acid (SA) (Malamy et al., 1990; Metraux et al., 1990; Ward et al., 1991).

Methods for inducing the HR in infected plants have been described. For example, Lam, E. et al., U.S. Pat. No. 5,629,470, have described a process for providing higher plants with enhanced resistance to pathogenic attack by one or more plant pathogens by transforming cells of the plants with the bacterio-opsin (bO) gene.

In view of the enormous economic impact of infectious diseases on agricultural production, a need continues to exist for transgenic plants having generalized resistance to pathogenic infections.

SUMMARY OF THE INVENTION

In accordance with the present invention, transgenic plants that have been stably transformed with the 2b gene of cucumovirus or an active fragment thereof have been found to possess systemic resistance to pathogenic infectious agents, such as viruses. The protein encoded by this gene activates strong disease resistance responses in host plants.

A further aspect of the invention relates to seeds and propagating parts of transgenic plants stably transformed with a cucumovirus 2b gene or an active fragment thereof. The invention further provides methods and vectors for introducing the cucumovirus 2b gene into plants.

BRIEF DESCRIPTION OF THE DRAWING

FIG. 1 illustrates the structural features and genome organization of the chimeric viral RNA transcripts from plasmids pTMV-t2b and pPVX-t2b.

FIG. 2 is a Northern blot hybridization showing the effect of the 2b gene on expression of the pathogenesis-related protein in leaves of tobacco plants infected with tobacco mosaic virus carrying the 2b gene.

DETAILED DESCRIPTION OF THE INVENTION

Cucumber mosaic virus (CMV) belongs to a virus genus called Cucumovirus which also includes tomato aspermy virus (TAV). Cucumovirus contains a tripartite single-stranded RNA genome that encodes five genes: 1a, 2a, 2b, 3a and coat protein. The identification and functional analysis of the 2b gene have been described in previous publications. (Ding et al., 1994; 1995; 1996). It has been demonstrated that the 2b gene encoded by the cucumoviruses is important for both systemic virus spread and virulence determination. The ribonucleotide sequence of the 2b gene is provided in SEQ ID NO. 1.

It has been discovered that when the 2b gene is expressed separately from the genome of cucumoviruses, it activates strong resistance responses in a variety of plant species upon infection with a pathogenic virus. These responses include induction of pathogenesis-related proteins and formation of necrotic lesions which eliminate the invading pathogens. Thus, in one aspect, the present invention relates to a transgenic plant stably transformed with a cucumovirus 2b gene or active fragment thereof operatively linked to a promoter that is capable of effecting expression of said gene in said plant when said plant is infected with a pathogenic organism. The cucumovirus 2b gene used for producing disease-resistant plants advantageously is one to which the nucleic acid of SEQ ID NO. 1 will hybridize under stringent conditions.

In a related aspect, the present invention provides methods for rendering a plant resistant to disease caused by an infectious pathogenic agent, which comprises stably transforming the plant with a cucumovirus 2b gene or active fragment thereof operatively linked to a plant-active promoter that is capable of effecting expression of the gene in the plant when said plant is infected with a pathogenic organism. In a further aspect, the invention provides an expression vector comprising a cucumovirus 2b gene or active fragment thereof operably linked to a plant-active promoter.

Mutational analysis has confirmed that the 2b gene is responsible for the resistance response. Point mutations in the gene have been shown to render it non-functional and abolish the ability of the gene to activate the resistance response. In addition, it has been found that the C-terminal 26-amino acid and 45-amino acid sequences of the gene are essential for its disease-resistance function, although the codons encoding the four C-terminal amino acids can be removed without losing activity. Transfer of the codons encoding the C-terminal 26 amino acids and the C-terminal 45 amino acids of the tomato aspermy virus 2b gene to the corresponding regions of the inactive cucumber mosaic virus 2b gene does not yield an active chimeric gene; therefore, the N-terminal portion of the protein also appears to contain one or more domains that are essential for resistance activation. Further routine gene mapping experimentation will reveal the active domains of the 2b gene. Accordingly, the invention relates to transgenic plants and vectors that contain an active fragment of the 2b gene.

The 2b gene or its active fragment (hereinafter, the "2b gene") may be introduced into plants using conventional vectors and procedures. Generally, such techniques involve inserting the 2b gene into an expression vector which contains the necessary elements for the transcription and translation of the inserted coding sequences and one or more marker sequences to facilitate selection of transformed cells or plants.

A number of plant-active promoters are known in the art and may be used to effect expression of the nucleic acid sequences disclosed herein. Constitutive promoters, such as the nos promoter or the 35S promoter of cauliflower mosaic virus, may be used; however, constitutive expression may be harmful to the transgenic plants. Accordingly, inducible promoters, especially pathogen-inducible promoters, such as pathogenesis-related protein promoters are preferred.

Once the 2b gene has been cloned into an expression vector, it may be introduced into a plant cell using conventional transformation procedures. The term "plant cell" is intended to encompass any cell derived from a plant including undifferentiated tissues such as callus and suspension cultures, as well as plant seeds, pollen or plant embryos. Plant tissues suitable transformation include leaf tissues, root tissues, meristems, protoplasts, hypocotyls, cotyledons, scutellum, shoot apex, root, immature embryo, pollen, and anther.

One technique for transforming plants is by contacting tissue of such plants with an inoculum of a bacterium transformed with a vector comprising the 2b gene in accordance with the present invention. Generally, this procedure involves inoculating the plant tissue with a suspension of bacteria and incubating the tissue for 48 to 72 hours on regeneration medium without antibiotics at 25–28° C.

Bacteria from the genus Agrobacterium can be utilized advantageously to transform plant cells. Suitable species of such bacteria include *Agrobacterium tumefaciens* and *Agrobacterium rhizogens*. *Agrobacterium tumefaciens* (e.g., strains LBA4404 or EHA105) is particularly useful due to its well-known ability to transform plants.

Another approach to transforming plant cells with the nucleic acid of this invention involves propelling inert or biologically active particles into plant cells. This technique is disclosed in U.S. Pat. Nos. 4,945,050, 5,036,006 and 5,100,792 all to Sanford et. al., which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector comprising the 2b gene. Biologically active particles (e.g., dried yeast cells, dried bacterium or a bacteriophage, each containing DNA sought to be introduced) can also be propelled into a plant cell tissue.

Another method of transforming plant cells is the electroporation method. This method involves mixing the protoplasts and the desired DNA and forming holes in the cell membranes by electric pulse so as to introduce the DNA into the cells, thereby transforming the cells. This method currently has high reproducibility and various genes have been introduced into monocotyledons, especially rice plants by this method (Toriyama et. al., 1988, Shimamoto et al., 1989 and Rhodes et al., 1988).

Similar to the electroporation method is a method in which the desired gene and protoplasts are mixed and the mixture is treated with polyethylene glycol ("PEG"), thereby introducing the gene into the protoplasts. This method is different from the electroporation method in that PEG is used instead of an electric pulse (Zhang W. et. al., 1988, Datta et al., 1990 and Christou et al., 1991).

Other methods include 1) culturing seeds or embryos with nucleic acids (Topfer R. et al., 1989, Ledoux et al., 1974) 2) treatment of pollen tube, (Luo et al., 1988) 3) liposome method (Caboche, 1990) and 4) the microinjection method (Neuhaus G. et al., 1987).

Known methods for regenerating plants from transformed plant cells may be used in preparing transgenic plants of the present invention. Generally, explants, callus tissues or suspension cultures can be exposed to the appropriate chemical environment (e.g., cytokinin and auxin) so the newly grown cells can differentiate and give rise to embryos which then regenerate into roots and shoots.

The 2b gene is useful in enhancing resistance to disease-causing pathogens in both monocotyledonous plants ("monocots") and dicotyledonous plants ("dicots"), such as corn, wheat, rice, millet, oat, barley, sorghum, sunflower, sweet potato, alfalfa, sugar beet, brassica species, tomato, pepper, soybean, tobacco, melon, squash, potato, peanut, pea, cotton or cacao.

The invention is further illustrated by the following examples, which are not intended to be limiting.

EXAMPLES

Example 1

(Vector Construction)

Several efficient in planta expression systems based on plant RNA viruses have been developed in recent years. The vectors based on tobacco mosaic virus (TMV) (U.S. Pat. No. 5,589,367) and potato virus X (PVX; Chapman et al., 1992) were used in this work for expressing the 2b genes of cucumoviruses. FIG. 1 shows the structural features of the chimeric viruses (TMV-t2b and PVX-t2b) that were constructed. The coding sequence of the 2b gene of TAV (SEQ ID NO. 1, encoding 95 amino acids) was prepared by PCR amplification of the TAV ORF 2b coding sequence (nucleotides 2447–2734 of RNA2) from pQCD2qt (Ding et al., 1996) using the Pfu DNA polymerase (Stratagene). This sequence was inserted into the genome of TMV and PVX upstream of the respective coat protein (CP) gene. The PCR fragment was blunt-end cloned at the PmeI site of a TMV vector, known as pTMV-30B, to yield TMV-t2b (FIG. 1). The TAV insert in TMV-t2b was excised as an AgeI - XhoI fragment (see FIG. 1), and this fragment was end-filled and cloned into ClaI-digested and end-filled pPC2S (an expression vector based on potato virus X (Chapman et al., 1992)) to produce PVX-t2b. The 2b gene expression was controlled by independent promoters (arrows labelled as 1 and 3 in FIG. 1) which are recognized only by the respective RNA-dependent RNA polymerase encoded by TMV or PVX.

The 2b-expressing derivatives of TMV or PVX (TMV-t2b and PVX-t2b) were used to infect plants and the functional role of the 2b gene was inferred from differences in the induced plant responses between the wild type and its 2b-expressing derivative.

Example 2

(Resistance in *Nicotiana tobacum* Samsun)

Figure 2:
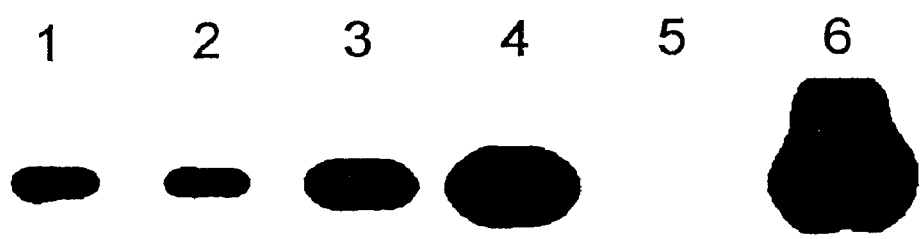

TMV-t2b induced a typical hypersensitive response (HR) in Samsun (nn) tobacco plants. Plasmids pTMV-30B, pPC2S and their derivatives were linearized and transcribed in vitro as described (Chapman et al., 1992) in the presence of the cap analog (NEB) using the T7 RNA polymerase (Promega). The capped RNA transcripts were inoculated mechanically onto fully developed leaves of *Nicotiana tabacum* cv Samsun (nn). The plants were incubated in the Conviron growth chambers (24° C. constant, 75% humidity and 16 hours light/8 hours dark). Local necrotic lesions appeared on the inoculated leaves about 4 days after inoculation and the rest of the plant was symptom-free for as long as observations were made (5 weeks). The failure of TMV-t2b to spread systemically in Samsun (nn) plants was further confirmed by Northern blot analysis which detected no accumulation of viral RNAs in upper uninoculated leaves. Furthermore, transcription of the mRNAs for pathogenesis-related (PR) protein 1 (PR-1), PR-3 and PR-5 was induced in the inoculated leaves. See FIG. 2, which is a Northern blot for leaves of plants challenged with TMV-t2b or TMV. Northern blot hybridization was performed using PR-1a cDNA as a probe (obtained by PCR amplification from tobacco plants based on the sequence disclosed by Cornelissen, B. J. et al. (1987)). Total RNAs extracted from plants 5 days (lane 1), 7 days (lane 2), 10 days (lane 3), and 13 days (lane 4) showed increasing expression of PR-1. Lanes 5 and 6 were infected with wild-type TMV; however, the tobacco genotype was nn for lane 5 and NN for lane 6.

These results showed that the Samsun (nn) tobacco plants were resistant to TMV-t2b and that challenge inoculation by TMV-t2b induced the expression of both the morphological (local necrotic lesions) and molecular (PR protein induction) markers of HR in the plants.

It is known that *N. tabacum* Samsun (nn) tobacco contains no resistance gene specific to TMV, and this is confirmed in this study that when infected with the vector TMV-30B alone, the tobacco plants developed systemic mosaic symptoms and no induction of the PR genes was observed. Thus, it is concluded that the resistance responses of the tobacco plants to TMV-t2b challenge is due to the in cis expression of the TAV 2b gene from the TMV genome.

Example 3

(Demonstration that the 2b Gene is Responsible for Resistance)

Two mutants of TMV-t2b, each containing point mutations to disrupt the open reading frame 2b, were constructed. TMV-tΔ2b1 (SEQ ID NO. 2) is predicted not to translate any of the 2b protein in infected plants. In plants infected with TMV-tΔ2b2 (SEQ ID NO. 3), however, a truncated 2b protein missing the C-terminal 52 amino acid residues is expected to be expressed. Neither TMV-tΔ2b1 nor TMV-tΔ2b2 induced local necrotic lesions in the inoculated leaves and transcription of mRNAs for PR proteins was also not induced. Therefore, it is the TAV 2b protein that functions as the activator of resistance responses. The inserted TAV nucleotide sequence per se played no role in the HR elicitation. In addition, it appears that the C-terminal 52 amino acid sequence of the TAV 2b protein is essential for this activity (see below).

Example 4

(Determination of Resistance Activation Domain)

The 2b gene encoded by the Q strain of cucumber mosaic virus (CMV) (SEQ ID NO. 4) was similarly engineered to be expressed from the TMV genome. The derivative, called TMV-q2b, systemically infected Samsun tobacco plants, did not induce necrotic lesions on the inoculated leaves, nor did it induce transcription of mRNAs for PR proteins. This shows that, in contrast to the TAV 2b protein, the CMV 2b protein was inactive in resistance activation.

To map the domain important for resistance activation, the TAV 2b protein as encoded by TMV-t2b was progressively replaced from the C-terminus by the structurally equivalent regions of the CMV 2b protein. Infectivity assays showed that replacing the C-terminal four amino acids of the TAV 2b protein retained its HR triggering activity. However, the replacement of the C-terminal 26 or 45 amino acids of the TAV 2b protein abolished its ability to trigger HR. This indicates that the C-terminal 26 amino acids of the TAV 2b protein is essential for resistance activation in tobacco plants, although the codons encoding the four C-terminal amino acids can be removed without losing activity. Transfer of the codons encoding the C-terminal 26 amino acids and the C-terminal 45 amino acids of the tomato aspermy virus 2b gene to the corresponding regions of the inactive cucumber mosaic virus 2b gene does not yield an active chimeric gene; therefore, the N-terminal portion of the protein also appears to contain one or more domains that are essential for resistance activation.

Example 5

(Resistance in Other Plant Species)

Both *Nicotiana benthamiana* and *Physalis floridana* plants are similar to the Samsun tobacco in that they are susceptible to TMV, and the infected plants do not develop HR. Infectivity assays showed that challenge inoculation with TMV-t2b induced typical local necrotic lesions in the inoculated leaves of both *Nicotiana benthamiana* and *Physalis floridana* plants, while the uninfected parts of the plants remained symptom-free. These results suggest that the TAV 2b gene is also capable of activating resistance in these plant species against TMV. The fact that the TAV 2b gene can activate resistance against TMV in three different plant species of two genera suggests that it will function similarly in a wide range of host species.

Example 6

(Resistance Against Potato Virus X)

Both Samsun (nn) and Xanthi-nc (NN) tobacco (N. tabacum) plants are fully susceptible to potato virus X (PVX) and to the RNA transcripts from the PVX-based vector (pPC2S) (Chapman et al., 1992). However, inoculation with the PVX-t2b transcripts induced HR in leaves of both tobacco varieties. The necrotic lesions induced by PVX-t2b infection were essentially identical to those induced by TMV-t2b on the Samsun (nn) plants. In addition, Northern blot analysis showed that transcription of the PR genes was also induced in plants challenged with PVX-t2b, but not with PVX or the PVX vector alone. Thus, the TAV 2b gene expression in cis from the PVX genome is also capable of triggering the resistance responses in tobacco plants containing no specific resistance gene to PVX.

TMV and PVX are distinct plant RNA viruses of different virus genera and the encoded proteins of the two viruses have minimal sequence similarities. Therefore, it is less likely that the resistance activation by the TAV 2b gene requires specific interaction with any of the proteins encoded by the two viral vectors. These results suggests a possibility that the TAV 2b gene will be able to activate resistance mechanisms against a wide range of plant pathogens.

Both the wild-type TAV (Ding et al., 1994) and the CMV/TAV chimera CMV-qt (Ding et al., 1996) encode the TAV 2b gene which is expressed at high levels in infected plants (Shi et al., 1997). It has been shown previously that all three plant species used in this work are fully susceptible to TAV and CMV-qt (Ding et al., 1996), suggesting that these plant species do not contain a resistance gene that recognizes the TAV 2b gene. This result indicates that the resistance activation activity of the TAV 2b gene is not constitutive in these plant species and may require an induction event such as infection with certain virulent pathogens (e.g., TMV and PVX). This property distinguishes the TAV 2b gene from the known avirulence genes encoded by plant pathogens.

REFERENCES

Caboche (1990). *Physiol. Plant.* 79:173–176.

Chapman, S., Kavanagh, T. and Baulcombe, D. (1992) Potato virus X as a vector for gene expression in Dlants. *Plant J.,* 2, 549–557.

Christou et al. (1991) *Bio/Technology* 9:957–962.

Cornelissen, B. J. et al. (1987). Structure of tobacco genes encoding pathogenesis-related proteins from the PR-1 group. *Nucleic Acids Research,* 15, 6799–6811.

Datta et al. (1990) *Bio/Technol.* 8:736–740.

Ding, S. W., Anderson, B. J., Haase, H. R. and Symons, R. H. (1994). New overlapping gene encoded by the cucumber mosaic virus genome. *Virology,* 198, 593–601.

Ding, S. W., Li, W. X. and Symons, R. H. (1995). A naturally occurring hybrid gene encoded by a plant RNA virus facilitates long distance virus movement. *EMBO J.,* 14, 5762–5772.

Ding, S. W., Shi, B. J., Li, W. X. and Symons, R. H. (1996). An interspecies hybrid RNA virus is significantly more virulent than either parental virus. *Proc. Nat'l Acad. Sci. USA,* 93, 7470–7474.

Ledoux et al., (1974) *Nature,* 249:17–21)

Kumagai, M. H., Turpen, T. H., Weinezettl, N., Della-Cioppa, G., Turpen, A. M., Donson, J., Hilf, M. E., Grantham, G. L., Dawson, W. O., Chow, T. P., Piatak, M. and Grill, L. K. (1993). Rapid, high level expression of biologically active a-trichosanthin in transfected plants by an RNA viral vector. *Proc. Nat'l Acad. Sci. USA,* 90, 427–430.

Malamy, J., Henning, J., and Klessig, D. F. (1992). Temperature-dependent induction of salicylic acid and its conjugates during the resistance response to tobacco mosaic virus infection. *Plant Cell,* 4, 359–366.

Metraux, J. P., Singer, H., Rayals, J., Ward, E., Wyss-Benz, M., Gaudin, J., Raschdorf, K., Schmid, E., Blum, W., and Inverardi, B. (1990). Increase in salicylic acid at the onset of systemic acquired resistance in cucumber. *Science,* 250, 1004–1006.

Rhodes et al., (1988) *Science,* 240:204–207).

Ross, A. F. (1961). Systemic acquired resistance induced by localized virus infection in plants. *Virology,* 14, 340–358.

Shi, B. J., Ding, S. W. and Symons, R. H. (1997). In vivo expression of an overlapping gene encoded by the cucumoviruses. *J. Gen. Virol.,* 78, 237–241.

Shimamoto et al., (1989) *Nature,* 338:274–277

Topfer R. et al., (1989) *Plant Cell,* 1:133–139

Toriyama et. al., (1988) *Bio/Technol.,* 6:1072–1074

Ward, E. R., Uknes, S. J., Williams, S. C., Dincher, S. S., Widerhold, D. L., Alexander, D. C., Ahl-Goy, P., Metraux, J. P., and Ryals, J. A. (1991). Coordinate gene activity in response to agents taht induce systemic acquired resistance. *Plant Cell,* 3, 1085–1094.

Zhang W. et. al., (1988) *Theor. Appl. Genet.,* 76:835–840.

What is claimed is:

1. A transgenic plant stably transformed with a tomato aspermy virus 2b gene, or a fragment of said gene which confers a hypersensitive response in a plant transformed therewith, operably linked to a promoter that effects expression of said gene or said fragment in said plant when said plant is infected with a pathogenic organism, wherein said transgenic plant has enhanced resistance to said pathogenic organism compared to an untransformed plant.

2. The transgenic plant of claim 1, wherein the tomato aspermy virus 2b gene comprises the sequence of SEQ ID NO. 1.

3. The transgenic plant of claim 1, wherein the plant is stably transformed with the fragment of the tomato aspermy virus 2b gene.

4. The transgenic plant of claim 1, wherein the fragment comprises a nucleic acid sequence encoding at least the 45 C-terminal amino acids of the protein encoded by the tomato aspermy virus 2b gene.

5. The transgenic plant of claim 1, wherein the fragment does not contain the nucleic acid sequence encoding the 4 C-terminal amino acids of the protein encoded by the tomato aspermy virus 2b gene.

6. The transgenic plant of claim 1, wherein the promoter is a pathogen-inducible promoter that is inducible by the pathogenic organism.

7. The transgenic plant of claim 6, wherein the pathogen-inducible promoter is a PR protein gene promoter.

8. The transgenic plant of claim 1, which is corn, wheat, rice, millet, oat, barley, sorghum, sunflower, sweet potato, alfalfa, sugar beet, Brassica species, tomato, pepper, soybean, tobacco, melon, squash, potato, peanut, pea, cotton or cacao.

9. A seed of the transgenic plant of claim 1, 2, 3, 4, 5, 6, or 7.

10. A propagating part of the transgenic plant of claim 1, 2, 3, 4, 5, 6, or 7.

11. A method for enhancing the resistance of a plant to a disease caused by an infectious pathogenic agent, which comprises stably transforming plant with a tomato aspermy virus 2b gene, or a fragment of said gene which confers a hypersensitive response in a plant transformed therewith operatively linked to a promoter that effects expression of said gene or said fragment in said plant when said plant is infected with a pathogenic organism, wherein said plant has enhanced resistance to said pathogenic organism compared to an untransformed plant.

12. The method of claim 11, wherein the tomato aspermy virus 2b gene comprises the sequence of SEQ ID NO. 1.

13. The method of claim 11, wherein the plant is stably transformed with the fragment of the tomato aspermy virus 2b gene.

14. The method of claim 11, wherein the fragment comprises a nucleic acid sequence encoding at least the 45 C-terminal amino acids of the protein encoded by the tomato aspermy virus 2b gene.

15. The method of claim 11, wherein the fragment does not contain the nucleic acid sequence encoding the 4 C-terminal amino acids of the protein encoded by the tomato aspermy virus 2b gene.

16. The method of claim 11, wherein the promoter is a pathogen-inducible promoter that is inducible by the pathogenic organism.

17. An expression vector comprising a tomato aspermy virus 2b gene or fragment of said gene which confers a hypersensitive response in a plant transformed therewith, operably linked to a plant-active promoter.

18. The expression vector of claim 17, wherein the plant-active promoter is a pathogen-inducible promoter.

19. The expression vector of claim 18, wherein the pathogen-inducible promoter is a PR protein gene promoter.

* * * * *

```
                         SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
          (A) LENGTH: 328 base pairs
          (B) TYPE: nucleic acid
          (C) STRANDEDNESS: double
          (D) TOPOLOGY: linear (ii) MOLECULE TYPE: DNA (genomic)

(iii) HYPOTHETICAL: NO (iv) ANTI-SENSE: NO
```

(vi) ORIGINAL SOURCE:
    (A) ORGANISM: Tomato aspermy virus (vii) IMMEDIATE SOURCE:
    (B) CLONE: pTMV-30B (xi) SEQUENCE DESCRIPTION: SEQ ID NO:1:

```
ACCGTTAAGA AGAAGAAGAA TGGCAAGCAT CGAGATCCCT CTACACGAGA TCATTCGAAA      60
GTTGGAACGG ATGAATCAAA AGAAACAAGC ACAGAGGAAA CGACACAAAC TGAACCGCAA     120
GGAGCGGGGT CACAAAAGTC CAAGTGAACA AAGGCGATCG GAGTTATGGC ACGCGCGTCA     180
AGTTGAACTT TCTGCCATTA ATTCCGATAA TTCTTCAGAT GAGGGTACCA CTCTGTGTCG     240
CTTTGACACA TTTGGTTCCA AGTCTGATGC TATTTGTGAT CGCTCTGACT GGTGTCTCGA     300
TCAATGATTT CCGACCCTTC GTCGTCCG                                       328
```

(2) INFORMATION FOR SEQ ID NO:2:

(i) SEQUENCE CHARACTERISTICS:
    (A) LENGTH: 328 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Synthetic DNA"

(iii) HYPOTHETICAL: NO (iv) ANTI-SENSE: NO (vi) ORIGINAL SOURCE:
    (A) ORGANISM: Tomato aspermy virus (vii) IMMEDIATE SOURCE:
    (B) CLONE: pTAVd2b1

(xi) SEQUENCE DESCRIPTION: SEQ ID NO:2:

```
ACCGTTAAGA AGAAGTAGAA TGTAAAGCAT CGAGATCCCT CTACACGAGA TCATTCGAAA      60
GTTGGAACGG ATGAATCAAA AGAAACAAGC ACAGAGGAAA CGACACAAAC TGAACCGCAA     120
GGAGCGGGGT CACAAAAGTC CAAGTGAACA AAGGCGATCG GAGTTATGGC ACGCGCGTCA     180
AGTTGAACTT TCTGCCATTA ATTCCGATAA TTCTTCAGAT GAGGGTACCA CTCTGTGTCG     240
CTTTGACACA TTTGGTTCCA AGTCTGATGC TATTTGTGAT CGCTCTGACT GGTGTCTCGA     300
TCAATGATTT CCGACCCTTC GTCGTCCG                                       328
```

(2) INFORMATION FOR SEQ ID NO:3:

(i) SEQUENCE CHARACTERISTICS:
    (A) LENGTH: 328 base pairs
    (B) TYPE: nucleic acid
    (C) STRANDEDNESS: single
    (D) TOPOLOGY: linear (ii) MOLECULE TYPE: other nucleic acid
    (A) DESCRIPTION: /desc = "Synthetic DNA"

(iii) HYPOTHETICAL: NO (iv) ANTI-SENSE: NO (vi) ORIGINAL SOURCE:
    (A) ORGANISM: Tomato aspermy virus (vii) IMMEDIATE SOURCE:
    (B) CLONE: pTAVd2b2

(xi) SEQUENCE DESCRIPTION: SEQ ID NO:3:

```
ACCGTTAAGA AGAAGTAGAA TGTAAAGCAT CGAGATCCCT CTACACGAGA TCATTCGAAA      60

GTTGGAACGG ATGAATCAAA AGAAACAAGC ACAGAGGAAA CGACACAAAC TGAACCGCAA     120

GGAGCGGGGT CACAAAAGTC CAAGTGAATA AAGGTGATCG GAGTTATGGC ACGCGCGTCA     180

AGTTGAACTT TCTGCCATTA ATTCCGATAA TTCTTCAGAT GAGGGTACCA CTCTGTGTCG     240

CTTTGACACA TTTGGTTCCA AGTCTGATGC TATTTGTGAT CGCTCTGACT GGTGTCTCGA     300

TCAATGATTT CCGACCCTTC GTCGTCCG                                        328

(2) INFORMATION FOR SEQ ID NO:4:

(i) SEQUENCE CHARACTERISTICS:
        (A) LENGTH: 504 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
         (A) ORGANISM: Cucumber mosaic virus (vii) IMMEDIATE SOURCE:
          (B) CLONE: pCMV2b (xi) SEQUENCE DESCRIPTION: SEQ ID NO:4:

GATCCATGGA TGTGTTGACA GTAGTGGTGT CGACCGCCGA CCTCCACTTA GCCAATTTGC      60

AGGAGGTGAA ACGTCGAAGA CGAAGGTCTC ACGTCAGAAA CCGGCGAGCG AGGGGTTACA     120

AAAGTCCCAG CGAGAGAGCG CGATCTATAG CGAGACTTTT CCAGATGTTA CCATTCCACG     180

GAGTAGATCC CGTGGATTGG TTTCCTGATG TCGTTCGCTC TCCGTCCGTT ACCAGCCTTG     240

TTTCTTATGA ATCTTTTGAT GATACTGATT GGTTTGCTGG TAACGAATGG GCCGAAGGGT     300

CGTTTTGATT TCCGACCCTT CGTCGTCCGA AGACGTTAAA CTACGCTCTC TTTATTGCGA     360

GTGCTGAGTT GGTAGTTTGC TCTAAACTAT CTGAAGTCGC TAAATCCATT ACTGGTTGCG     420

AACGGGTTGT CCATCCAGCT TACGGCTAAA ATGGTCAGTC ATGCCCCAAA GGCATGCCGA     480

CACCCTACAG GGTTGTCGAG GTAC                                            504
```